US007975527B2

(12) United States Patent
Manahan

(10) Patent No.: US 7,975,527 B2
(45) Date of Patent: Jul. 12, 2011

(54) EXPLOSION INDICATORS FOR USE IN EXPLOSION-PROOF ENCLOSURES WITH CRITICAL EQUIPMENT

(75) Inventor: Joseph Michael Manahan, Manilus, NY (US)

(73) Assignee: Cooper Technologies Company, Houston, TX (US)

( * ) Notice: Subject to any disclaimer, the term of this patent is extended or adjusted under 35 U.S.C. 154(b) by 0 days.

(21) Appl. No.: 12/813,114

(22) Filed: Jun. 10, 2010

(65) Prior Publication Data

US 2010/0242830 A1 Sep. 30, 2010

Related U.S. Application Data

(62) Division of application No. 11/960,904, filed on Dec. 20, 2007, now Pat. No. 7,757,623.

(51) Int. Cl.
*G01N 33/22* (2006.01)
*G01L 5/00* (2006.01)
*G01L 5/14* (2006.01)
*G01K 3/00* (2006.01)

(52) U.S. Cl. ....... 73/35.14; 116/203; 116/212; 116/218; 116/272; 73/35.17; 374/106

(58) Field of Classification Search ................. 73/35.14, 73/35.17; 116/203, 212, 272, 281, 283, 218; 374/106
See application file for complete search history.

(56) References Cited

U.S. PATENT DOCUMENTS 1,692,012 A 11/1928 Wells ............ 116/216
2,764,979 A * 10/1956 Henderson ............ 604/200
2,805,523 A * 9/1957 Springer ............ 451/241
3,233,459 A 2/1966 Gleason et al. ............ 374/106
3,452,706 A * 7/1969 Vogt ............ 116/102
3,515,091 A 6/1970 Smith ............ 116/203
3,548,780 A * 12/1970 Kliewer ............ 116/218
3,559,615 A * 2/1971 Kliewer ............ 116/218
3,765,025 A 10/1973 Zietzke et al. ............ 346/7
3,965,741 A 6/1976 Wachtell et al. ............ 374/102
4,082,000 A * 4/1978 Volk ............ 374/106
4,143,617 A 3/1979 Youngren ............ 374/102
4,156,891 A 5/1979 Roche ............ 362/20
4,183,536 A 1/1980 Platt ............ 473/570
4,356,790 A * 11/1982 Gee ............ 116/218
4,362,121 A 12/1982 Pegram ............ 116/34 R
4,421,053 A * 12/1983 Volk ............ 116/218
4,445,456 A * 5/1984 Nelson ............ 116/268
4,512,278 A * 4/1985 Winther ............ 116/34 R
4,748,931 A * 6/1988 Volk ............ 116/218
4,789,922 A 12/1988 Cheshire ............ 362/158
5,027,740 A 7/1991 Kramer et al. ............ 16/34 R
5,144,112 A 9/1992 Wyatt et al. ............ 219/386
5,144,880 A * 9/1992 Schmit ............ 99/342
5,537,950 A * 7/1996 Ou-Yang ............ 116/218
5,616,157 A * 4/1997 Mead et al. ............ 96/421
5,821,695 A 10/1998 Vilanilam et al. ............ 315/58
5,918,262 A 6/1999 Sanford ............ 73/35.14
5,988,102 A * 11/1999 Volk et al. ............ 116/218
6,531,960 B1 3/2003 Gladstone et al. ............ 340/442
6,609,865 B2 8/2003 Daigneault ............ 411/13
(Continued)

*Primary Examiner* — Randy W Gibson
(74) *Attorney, Agent, or Firm* — King & Spalding LLP

(57) ABSTRACT

Indicator devices and systems are provided. Indicator devices include a sleeve, a dome-like transparent member, a connector body, and an indicator. In alternate embodiments, indicator devices include a sleeve and an indicator retained in the sleeve by a retaining ring and a latch held in place by a spring. Indicator systems include an indicator device coupled to an enclosure containing critical equipment.

20 Claims, 7 Drawing Sheets

U.S. PATENT DOCUMENTS

| | | | | |
|---|---|---|---|---|
| 6,639,190 | B2 | 10/2003 | Lerner | 219/445.1 |
| 6,651,834 | B2 * | 11/2003 | Wong | 215/260 |
| 6,700,100 | B2 | 3/2004 | Lerner | 219/445.1 |
| 6,848,389 | B1 | 2/2005 | Elsasser et al. | 116/203 |
| 6,911,903 | B2 | 6/2005 | Gladstone et al. | 340/442 |
| 7,013,833 | B2 | 3/2006 | Lemberger et al. | 116/34 R |
| 7,030,743 | B2 | 4/2006 | Morris | 340/442 |
| 7,112,766 | B2 | 9/2006 | Lerner | 219/445.1 |
| 7,204,199 | B2 * | 4/2007 | Ribi et al. | 116/218 |
| 7,528,737 | B2 | 5/2009 | Hedtke | 340/870.01 |
| 7,641,358 | B1 | 1/2010 | Smith et al. | 362/183 |
| 2003/0214816 | A1 | 11/2003 | Barlian et al. | |
| 2004/0146084 | A1 | 7/2004 | Hachtel et al. | 374/106 |
| 2005/0217558 | A1 | 10/2005 | Fitzer et al. | 116/203 |
| 2006/0220895 | A1 | 10/2006 | Arcaria et al. | 340/815.4 |
| 2007/0241916 | A1 | 10/2007 | Hedtke | 340/584 |
| 2009/0284381 | A1 | 11/2009 | Manahan | 340/590 |
| 2010/0039256 | A1 | 2/2010 | Manahan | 340/540 |
| 2010/0043695 | A1 | 2/2010 | Reichert | 116/207 |
| 2010/0163765 | A1 | 7/2010 | Gregoire | |
| 2010/0229784 | A1 * | 9/2010 | Bayne et al. | 116/203 |
| 2010/0275676 | A1 * | 11/2010 | King et al. | 73/35.14 |

* cited by examiner

EXPLOSION INDICATORS FOR USE IN EXPLOSION-PROOF ENCLOSURES WITH CRITICAL EQUIPMENT

CROSS-REFERENCE TO RELATED APPLICATIONS

This application is a divisional application of commonly-owned U.S. patent application Ser. No. 11/960,904, filed Dec. 20, 2007 now U.S. Pat. No. 7,757,623, entitled "Explosion Indicators for Use in Explosion-Proof Enclosures with Critical Equipment," which is incorporated by reference herein for all purposes.

BACKGROUND OF THE INVENTION

The present application relates to indicator devices for use with explosion-proof enclosures containing critical equipment. Under some circumstances, enclosed equipment may be damaged when subject to internal explosions, thus rendering the equipment faulty. Currently, there are no devices or methods of alerting a user that an internal explosion has occurred in equipment already equipped to withstand high pressures. As a result, in some instances, the equipment may continue to operate without maintenance under unsafe or faulty conditions and lead to further damage to the internal equipment, as well as damage to any downstream equipment connected to the internal equipment.

SUMMARY OF THE INVENTION

The present invention satisfies the above-described need by providing an indicator device having a sleeve, a dome-like transparent member having a cavity, a connector body, and an indicator. The sleeve is open at each end and includes a bore therein. The cavity of the transparent member is in communication with the sleeve bore and thereby creates a chamber, into which the indicator is placed. The connector body couples the sleeve to the transparent member, and may be a cylindrical unit or a guard unit. The indicator devices may also include a gasket positioned between the sleeve and the transparent member. In some embodiments, the transparent member may be a glass jewel.

Generally, the indicator responds to a temperature differential and/or pressure differential. In some instances, the indicator may be a material that changes color in response to a temperature differential and/or pressure differential, and may comprise fibers, high temperature plastics, pressure sensitive films, and combinations thereof. These indicators may include flame retardant material and/or brightly colored material, and in some embodiments, may be enclosed in a highly flammable material. In some embodiments, the indicator may be a capsule having a first compartment including a first chemical and a second compartment including a second chemical, separated by a partition. The partition may be an elastic membrane or a thin glass partition that reacts to a temperature differential and/or pressure differential so as to allow the first and second chemicals to mix and emit light. The first chemical may be a luminol, an oxalate, a derivative or salt thereof, or any combination thereof. In some embodiments, the first chemical is bis(2,4,5-trichlorophenyl-6-carbopentoxyphenyl)oxalate. The second chemical may be an oxidant. Furthermore, a fluorophore may be added to the first and/or second chemical.

An alternate embodiment of an indicator device of the present invention includes a sleeve and an indicator. The indicator may be a brightly-colored component and is retained in the sleeve by a retaining ring and a latch held in place by a spring. When the temperature differential or pressure differential is greater than the restrictive force of the spring, at least a portion of the indicator exits the sleeve.

Explosion indicator systems are also provided, wherein an indicator device of the present invention is coupled to an enclosure containing critical equipment.

The features of the present invention will be readily apparent to those skilled in the art upon a reading of the description of the preferred embodiments that follows.

BRIEF DESCRIPTION OF THE DRAWINGS

The present invention may be better understood by reading the following description of non-limitative embodiments with reference to the attached drawings wherein like parts of each of the several figures are identified by the same referenced characters, and which are briefly described as follows.

Figure 1A:
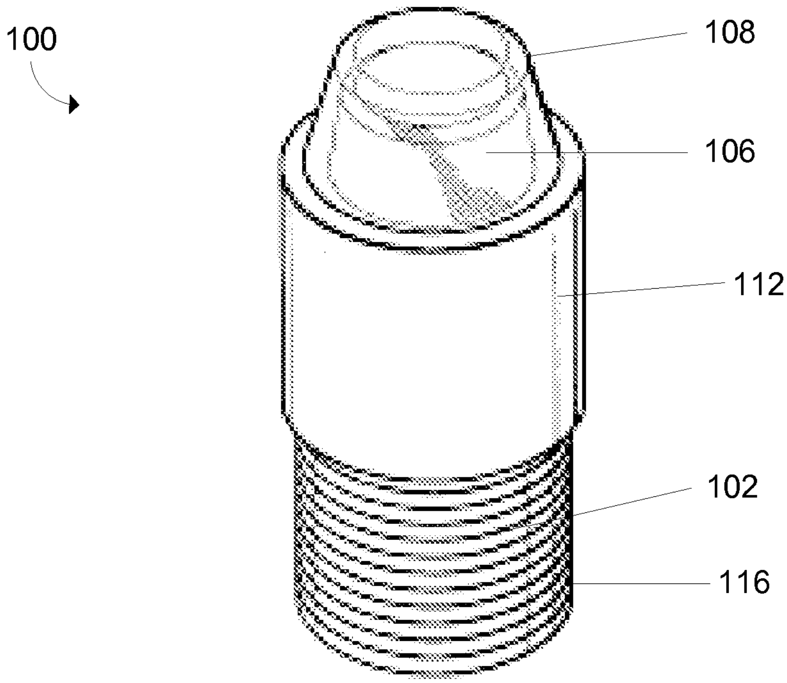
FIG. 1A is a perspective view of an embodiment of an explosion indicator device.
Figure 1B:
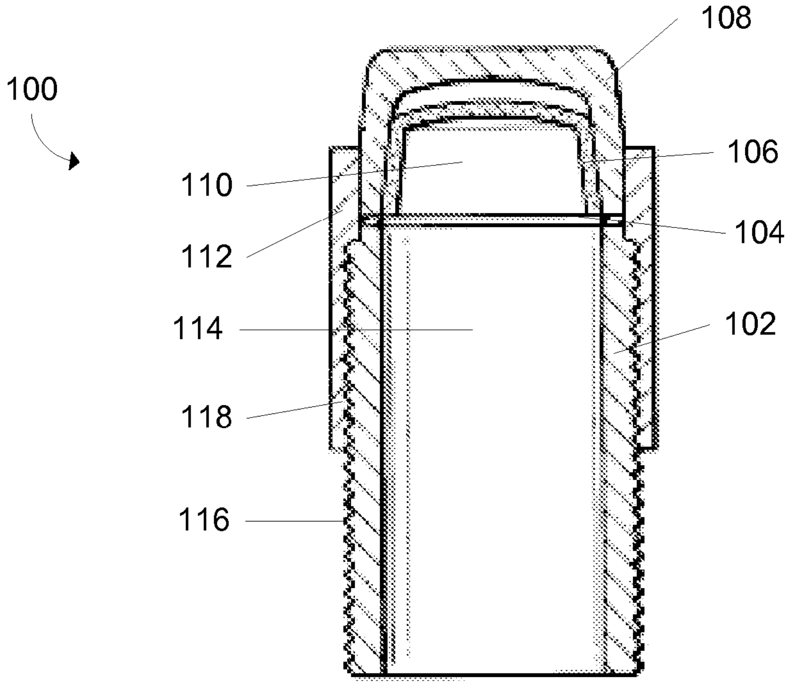
FIG. 1B is a sectional view of the explosion indicator device of FIG. 1A.
Figure 1C:
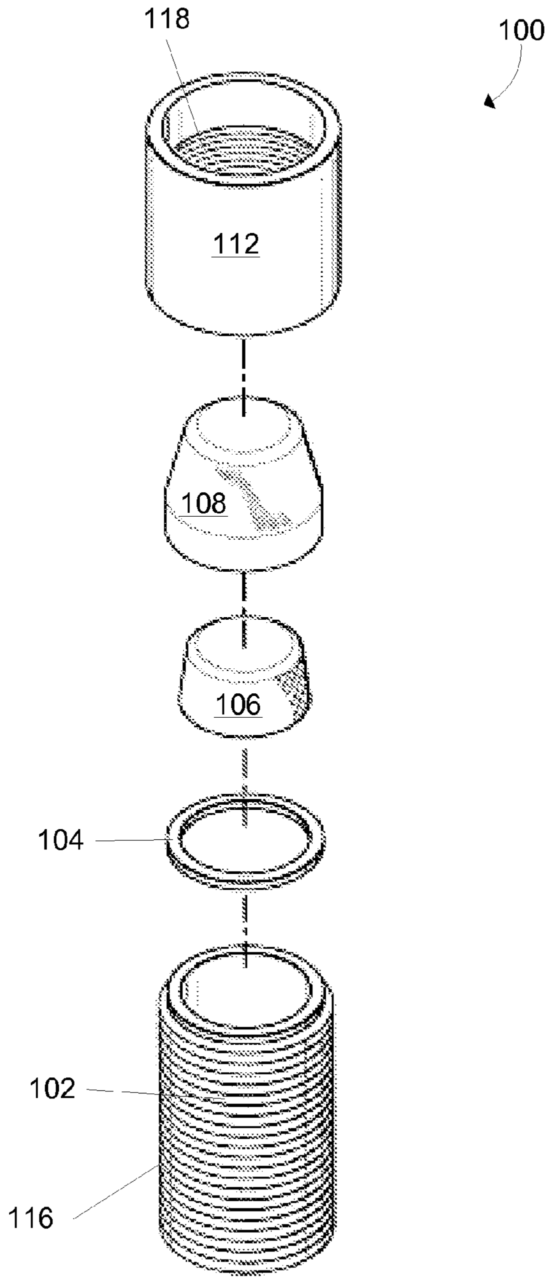
FIG. 1C is a perspective view of the elements of the explosion indicator device of FIG. 1A.
Figure 1D:
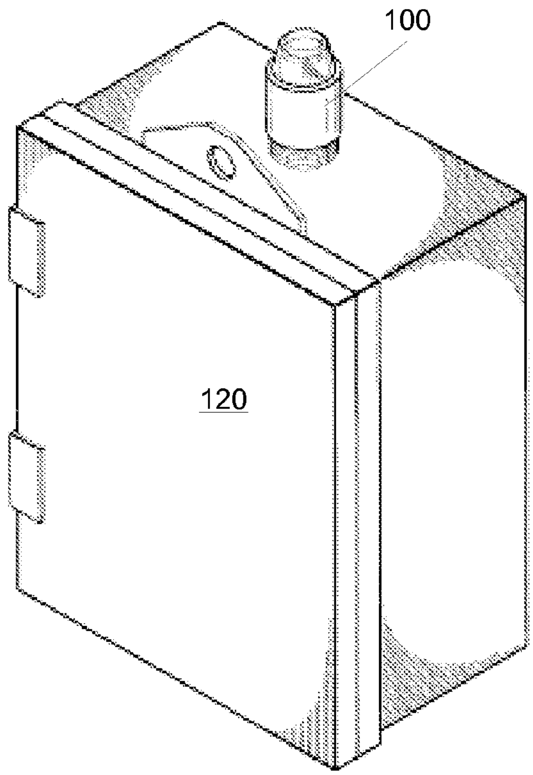
FIG. 1D is a perspective view of the explosion indicator device of FIG. 1A mounted to an explosion-proof enclosure containing critical equipment.

It is to be noted, however, that the appended drawings illustrate only typical embodiments of this invention and are therefore not to be considered limiting of its scope, as the invention may admit to other equally effective embodiments.

DETAILED DESCRIPTION OF THE INVENTION

The present application relates to indicator devices. More particularly, the present application relates to explosion indicator devices for use with explosion-proof enclosures containing critical equipment. The indicator devices of the present invention are of simple construction and assembled from easily replaceable parts, therefore possibly minimizing costs of servicing damaged or used devices.

Referring to FIGS. 1A-1D, an exemplary embodiment of an indicator device 100 includes a sleeve 102, a gasket 104, a fiber insert 106, a glass jewel 108 having a cavity 110, and a connector body 112. Sleeve 102 is open at each end and includes a bore 114 therein. Cavity 110 and bore 114 are in communication so as to create a chamber within which the fiber insert 106 is positioned. Sleeve 102 includes exterior threads 116 which threadably engage with connector body 112 having interior threads 118 and an enclosure 120 having interior threads (not shown).

Figure 2A:
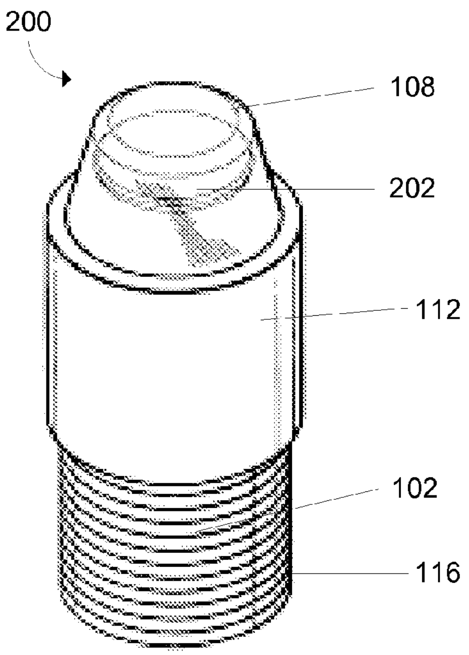
FIG. 2A is a perspective view of an embodiment of an explosion indicator device.
Figure 2B:
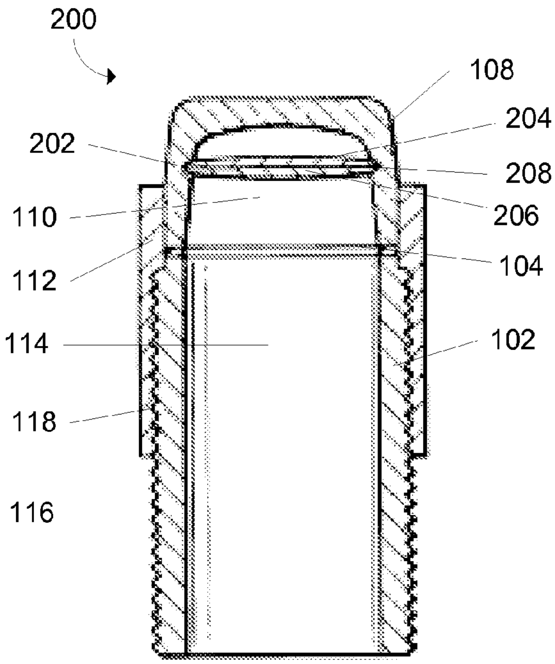
FIG. 2B is a sectional view of the explosion indicator device of FIG. 2A before activation.
Figure 2C:
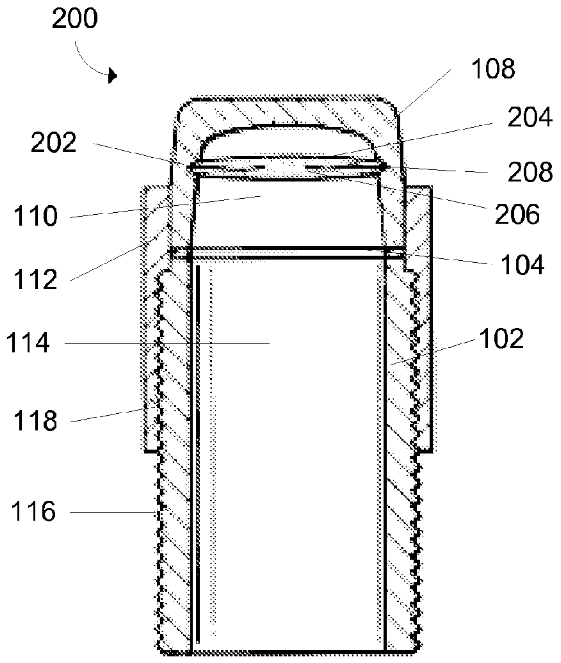
FIG. 2C is a sectional view of the explosion indicator device of FIG. 2A after activation.

Referring to FIGS. 2A-2C, an exemplary embodiment of an indicator device 200 includes a sleeve 102, a gasket 104, a capsule 202 having a first compartment 204 and a second compartment 206 separated by a partition 208, a glass jewel 108 having a cavity 110, and a connector body 112. Sleeve 102 is open at each end and includes a bore 114 therein. Cavity 110 and bore 114 are in communication so as to create a chamber within which the capsule 202 is positioned. Sleeve 102 includes exterior threads 116 which threadably engage with connector body 112 having interior threads 118 and an enclosure (not shown) similar to that in FIG. 1D. As shown in FIG. 2C, when the capsule 202 is activated, the partition 208 reacts so as to allow the contents of first compartment 204 and contents of second compartment 206 to mix.

Figure 3A:
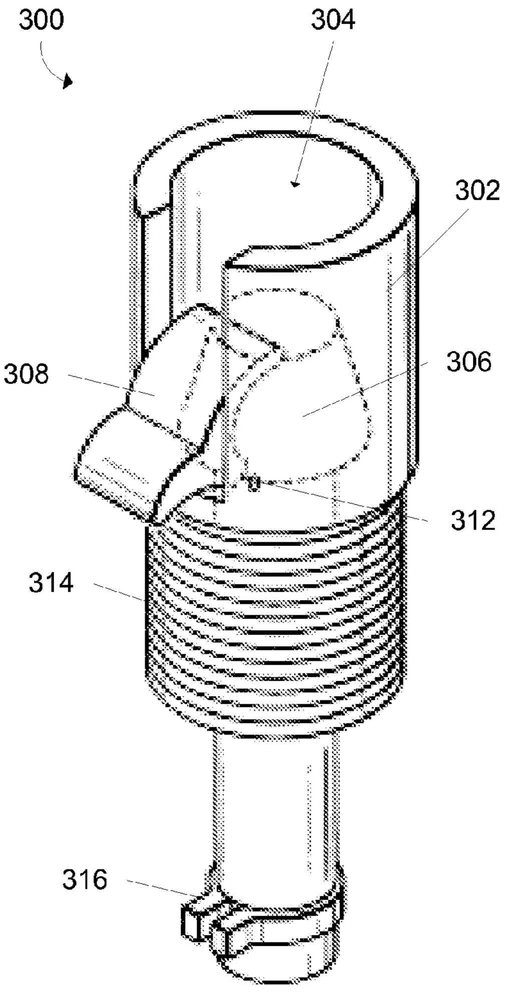
FIG. 3A is a perspective view of an embodiment of an explosion indicator device before activation.
Figure 3B:
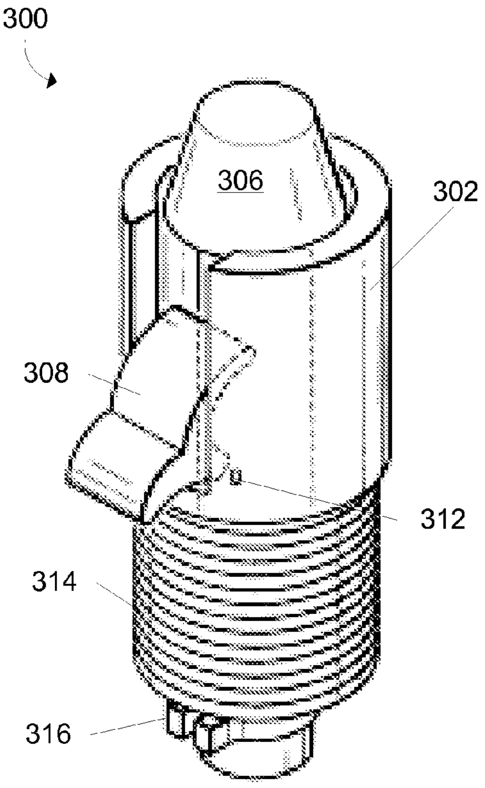
FIG. 3B is a perspective view of the explosion indicator device of FIG. 3A after activation.
Figure 3C:
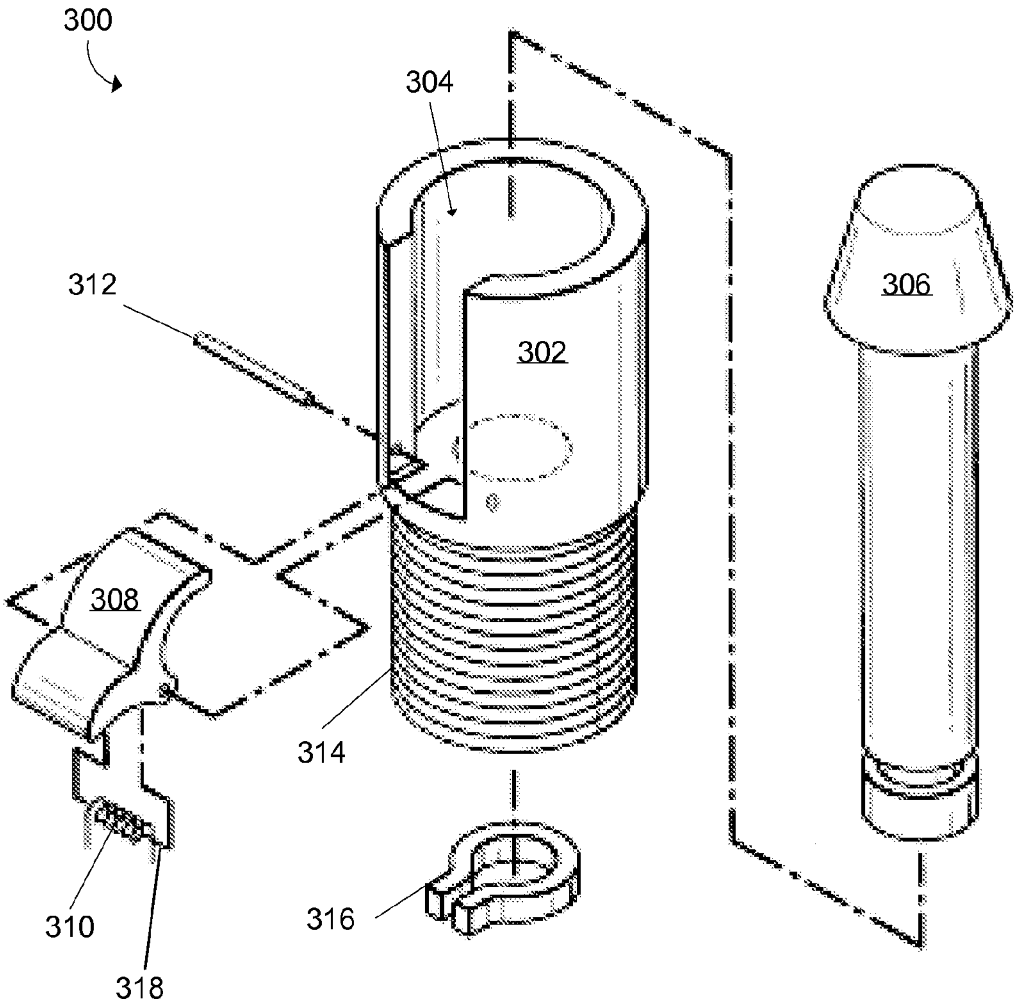
FIG. 3C is a perspective view of the elements of the explosion indicator device of FIG. 3A.
Figure 3D:
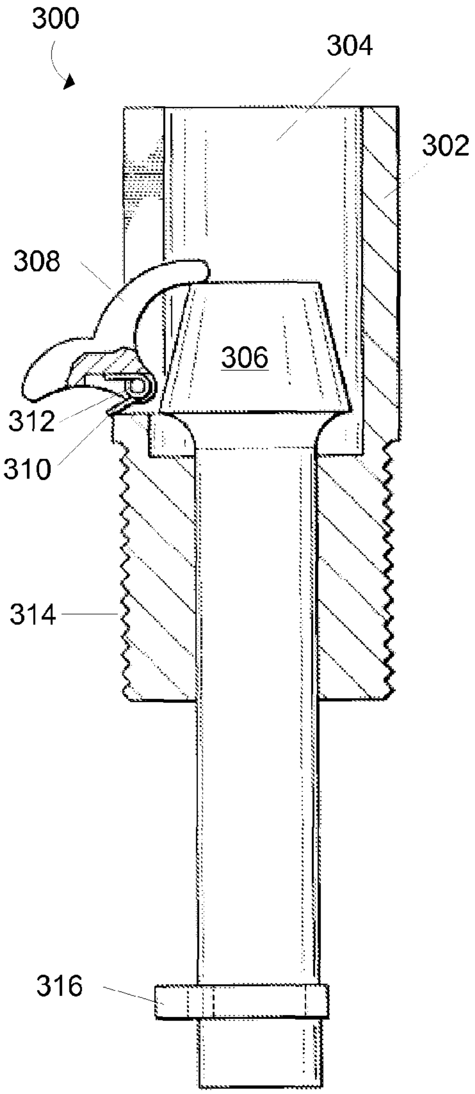
FIG. 3D is a sectional view of the explosion indicator device of FIG. 3A before activation.
Figure 3E:
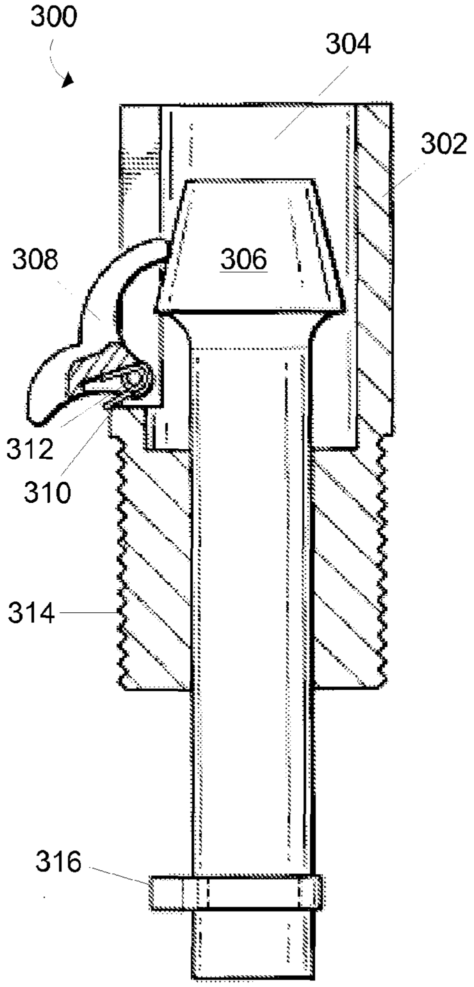
FIG. 3E is a sectional view of the explosion indicator device of FIG. 3A as the device is being activated.
Figure 3F:
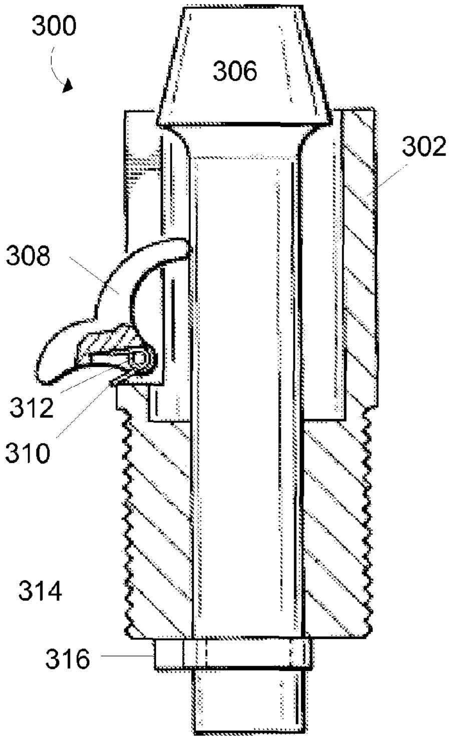
FIG. 3F is a sectional view of the explosion indicator device of FIG. 3A after activation.
Figure 3G:
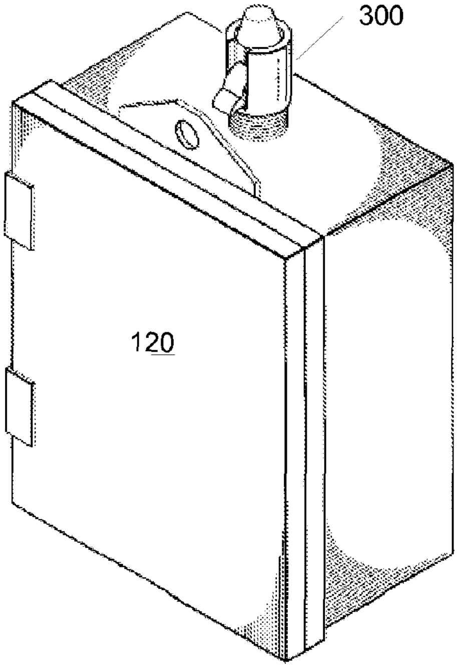
FIG. 3G is a perspective view of the explosion indicator device of FIG. 3A mounted to an explosion-proof enclosure containing critical equipment.

Referring to FIGS. 3A-3G, an exemplary embodiment of an indicator device 300 includes a sleeve 302 open at each end and having an opening in a portion of the sleeve wall, and having a bore 304 therein, and a brightly colored component 306 retained in sleeve 302 by a latch 308 held in place by a pivot spring 310 and pin 312. The pivot spring 310 includes a central axis 318 (FIG. 3C) extending through a center of and along a length of the pivot spring 310. Sleeve 302 includes exterior threads 314 which threadably engages with enclosure 120 having interior threads (not shown). When the pressure differential is greater than the restrictive force of the pivot spring 310, the latch 308 pivots about the central axis 318 from a first position (FIG. 3D) to a second position (FIG. 3E). The indicator device 300 is activated and at least a portion of the brightly colored component 306 exits the top portion of sleeve 302, as indicated by FIGS. 3B and 3F, and retaining ring 316 prevents brightly colored component 306 from completely exiting the sleeve 302.

Figure 4:
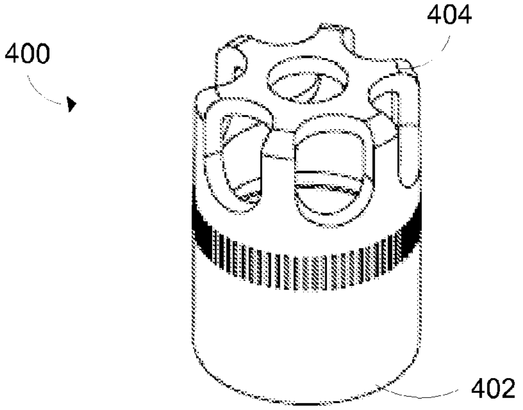
FIG. 4 is a perspective view of a guard unit.

Referring to FIG. 4, an exemplary embodiment of a guard unit 400 that may be used to replace connector body 112 in indicator devices 100 and 200. Guard unit 400 is open at one end 402 and at least partially open at a second end 404, and includes a bore therein. Guard unit 400 includes interior threads (not shown) for threadably engaging a sleeve 102 of indicator devices 100 and 200. Second end 404 protects glass jewel 108, while allowing a user at least partial visual sight of glass jewel 108.

Generally, the indicator devices of the present invention include a sleeve open at each end and having a bore therein, a dome-like transparent member having a cavity, a connector body, and an indicator. The transparent member is coupled to the sleeve by the connector body such that the cavity is in communication with the bore and thereby creating a chamber, and the indicator is positioned within the chamber. In some embodiments, the indicator device may further include a gasket, seal, or other sealing device positioned between the sleeve and the transparent member. The materials of construction for the indicator devices of the present invention is dependent on a variety of factors, such as the operating temperature and pressure, the particular application, equipment conditions, and the like, which will be recognizable by a person skilled in the art.

The sleeve of the indicator devices of the present invention may be made of any material that can withstand the presence of flammable vapors, gases, or highly combustible dusts. Suitable examples of sleeve material include, but are not limited to, brass, stainless steel, aluminum, or plastics appropriate for hazardous applications. The sleeve construction should provide integrity to the indicator device. For example, a threaded portion may be included in the sleeve to provide a flame-resistant exit path in the case of an explosion.

Suitable examples of the dome-like transparent member include, but are not limited to, glass jewels, transparent plastic materials, or other means of visualizing an indicator. In some embodiments, the dome-like transparent member may be clear. In some embodiments, the dome-like transparent member may be colored so as to enhance visually any light emitted by the indicator within.

The connector body of the indicator devices of the present invention may be made of any material that can withstand the presence of flammable vapors, gases, or highly combustible dusts. Suitable examples of connector body material include, but are not limited to, those suitable for environmental exposure. The connector body is a mechanical means to connect the transparent member to the sleeve. The connector body may also provide an explosion proof joint between the transparent member and connector body via a flat flamepath, and/or an explosion proof joint within the body via a threaded flamepath. Furthermore, the connector body may be a guard unit for protecting the dome-like transparent member to achieve higher impact standards.

The indicators of the present invention are activated in response to a temperature differential, pressure differential, or both. In some embodiments, the indicator may include a material that changes color in response to a temperature differential and/or pressure differential. The material may be in the form of an insert that is placed in cavity of the indicator devices of the present invention. In some embodiments, the material may include fibers, high temperature plastics, or pressure sensitive films that discolor in response to a temperature differential and/or pressure differential. Suitable examples of these materials include, but are not limited to, flame retardant material, brightly colored material, and combinations thereof. Examples of suitable pressure sensitive films include, but are not limited to, those described in U.S. Pat. No. 6,442,316. In some embodiments, the materials may be enclosed in a highly flammable material, such as kapok fibers. Other materials and configurations for the insert will also be apparent to those of ordinary skill in the art and are considered to be within the scope of the present invention.

In some embodiments, the indicator may be in the form of a capsule having a first compartment and a second compartment separated by a partition that reacts to a temperature and/or pressure differential. In some embodiments, the indicator may have more than two compartments separated by partitions that react to a temperature and/or pressure differential. The partition may be an elastic membrane having a cross-section designed to fail under a desired circumstance, or may be a thin glass partition capable of fracturing under pressure. Other configurations for the partition will also be apparent to those of ordinary skill in the art and are considered to be within the scope of the present invention. The compartments may be equal in size, or of different sizes. The first compartment may include a first chemical and the second compartment may include a second chemical, wherein light is emitted when the first and second chemicals are mixed after the partition reacts. Suitable examples of the first chemical include, but are not limited to, luminols, oxalates, derivatives and salts thereof, and combinations thereof. Examples of suitable oxalates include, but are not limited to, bis(2,4,5-trichlorophenyl-6-carbopentoxyphenyl)oxalate. Suitable examples of the second chemical include, but are not limited to, oxidants. In some embodiments, a fluorophore may be further added to the first chemical and/or second chemical.

Suitable examples of fluorophores include, but are not limited to, 2,4-di-tert-butylphenyl 1,4,5,8-tetracarboxynaphthalene diamide (for red color) and 5,12-bis(phenylethynyl)naphthacene (for orange color). Other fluorophores will be apparent to those of ordinary skill in the art and are considered to be within the scope of the present invention.

In some embodiments, the indicator devices of the present invention may include a sleeve open at each end and having a bore formed therein and an indicator placed in the bore. The indicator is retained in the sleeve by a latch held in place by a spring and a retaining ring. Suitable examples of springs include, but are not limited to, pivot springs or living hinge springs. The spring may be constructed of any material that will not likely oxidize and impede performance of the device. In some embodiments, the spring may be constructed from stainless steel. In some embodiments, the indicator may be a brightly-colored component. When a temperature differential or pressure differential is greater than the restrictive force of the spring, the indicator device is activated and at least a portion of the indicator exits the sleeve.

In some embodiments, methods associated with indicator devices of the present invention include methods of providing a system for detecting a high stress event, including providing an enclosure coupled to an indicator device having a sleeve open at each end and having a bore therein, a dome-like transparent member having a cavity, a connector body, and an indicator, wherein the indicator is adapted to activate upon exposure to a temperature differential, pressure differential, or both. The transparent member is coupled to the sleeve by the connector body such that the cavity is in communication with the bore and thereby creating a chamber, and the indicator is positioned within the chamber. In some embodiments, activating the indicator comprises the indicator changing color. In other embodiments, the indicator is a capsule having a first compartment having a first chemical and a second compartment having a second chemical separated by a partition, and activating the indicator comprises the partition reacting so as to allow the first and second chemicals to mix so as to emit light.

In some embodiments, methods associated with indicator devices of the present invention include methods of providing a system for detecting a high stress event, including providing an enclosure coupled to an indicator device having a sleeve open at each end and having a bore formed therein, and an indicator placed in the bore and retained in the sleeve by a latch held in place by a spring and a retaining ring, wherein the indicator is adapted to activate upon exposure to a temperature differential, pressure differential, or both. In some embodiments, the indicator is a brightly-colored component. In some embodiments, activating the indicator includes at least a portion of the indicator exiting the sleeve when a temperature differential or pressure differential is greater than the restrictive force of the pivot spring.

Generally, systems of the present invention comprise an indicator device of the present invention coupled to an enclosure. The indicator devices of the present invention may have features that allow it to be easily coupled to an enclosure comprising equipment. For example, the sleeve may include outer threads adapted for threading engagement with complimentary threads formed in the interior of the enclosure wall. In another example, the indicator devices may include a highly machined flat surface that may be bolted or secured to a highly machined flat surface of an enclosure.

Therefore, the present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. While numerous changes may be made by those skilled in the art, such changes are encompassed within the spirit of this invention as defined by the appended claims. Furthermore, no limitations are intended to the details of construction or design herein shown, other than as described in the claims below. It is therefore evident that the particular illustrative embodiments disclosed above may be altered or modified and all such variations are considered within the scope and spirit of the present invention. The terms in the claims have their plain, ordinary meaning unless otherwise explicitly and clearly defined by the patentee.

What is claimed is:

1. An indicator device comprising:

a sleeve open at each end and having a bore formed therein; and an indicator placed in the bore, wherein the indicator is retained in the sleeve by a latch held in place by a spring, the spring having a central axis extending therethrough, wherein the latch is pivotable about the central axis.

2. The indicator device of claim 1, wherein the indicator is a brightly-colored component.

3. The indicator device of claim 1, wherein at least a portion of the indicator exits the sleeve when a pressure differential is greater than a restrictive force of the spring.

4. The indicator device of claim 1, wherein the latch engages a top portion of the indicator, wherein when a pressure differential is greater than a restrictive force of the spring, the latch disengages the top portion of the indicator and allows a portion of the top portion to exit the sleeve.

5. The indicator device of claim 1, further comprising a retaining mechanism that prevents the indicator from completely exiting the sleeve when a pressure differential is greater than a restrictive force of the spring.

6. The indicator device of claim 5, wherein the retaining mechanism is a retaining ring positioned around a bottom portion of the indicator.

7. The indicator device of claim 1, further comprising a guard unit coupled to the sleeve, wherein the guard unit has a cavity that is in communication with the bore to thereby create a chamber, wherein at least a portion of the indicator is disposed within the chamber when a pressure differential is greater than the restrictive force of the pivot spring, and wherein the indicator is visible through at least a portion of the guard unit when the indicator is disposed within the chamber.

8. The indicator device of claim 1, wherein the spring is a pivot spring or a living hinge spring.

9. A system comprising:

an enclosure; and an indicator device coupled to the enclosure, wherein the indicator device comprises:

a sleeve open at each end and having a bore formed therein; and an indicator placed in the bore, wherein the indicator is retained in the sleeve by a latch held in place by a spring, the spring having a central axis extending therethrough, wherein the latch is pivotable about the central axis.

10. The indicator device of claim 9, wherein the indicator is a brightly-colored component.

11. The indicator device of claim 9, wherein at least a portion of the indicator exits the sleeve when a pressure differential is greater than a restrictive force of the spring.

12. The indicator device of claim 9, wherein the latch engages a top portion of the indicator, wherein when a pressure differential is greater than a restrictive force of the spring, the latch disengages the top portion of the indicator and allows a portion of the top portion to exit the sleeve.

13. The indicator device of claim 9, further comprising a retaining mechanism that prevents the indicator from completely exiting the sleeve when a pressure differential is greater than a restrictive force of the spring.

14. The indicator device of claim 13, wherein the retaining mechanism is a retaining ring positioned around a bottom portion of the indicator.

15. The indicator device of claim 9, further comprising a guard unit coupled to the sleeve, wherein the guard unit has a cavity that is in communication with the bore to thereby create a chamber, wherein at least a portion of the indicator is disposed within the chamber when a pressure differential is greater than the restrictive force of the pivot spring, and wherein the indicator is visible through at least a portion of the guard unit when the indicator is disposed within the chamber.

16. The indicator device of claim 9, wherein the spring is a pivot spring or a living hinge spring.

17. An indicator device comprising:

a sleeve open at each end and having a bore formed therein; and an indicator placed in the bore, wherein the indicator is retained in the sleeve by a retaining ring and a latch held in place by a spring, the spring having a central axis extending therethrough, wherein the latch is pivotable about the central axis, and wherein at least a portion of the indicator exits the sleeve when a temperature differential is greater than a restrictive force of the spring.

18. The indicator device of claim 17, wherein the indicator is a brightly-colored component.

19. The indicator device of claim 17, wherein the latch engages a top portion of the indicator, wherein when the temperature differential is greater than the restrictive force of the spring, the latch disengages the top portion of the indicator and allows the portion of the top portion to exit the sleeve.

20. The indicator device of claim 17, wherein the retaining ring is positioned around a bottom portion of the indicator and prevents the indicator from completely exiting the sleeve when a temperature differential is greater than a restrictive force of the spring.

* * * * *